US011823800B2

(12) United States Patent
Wujek et al.

(10) Patent No.: US 11,823,800 B2
(45) Date of Patent: Nov. 21, 2023

(54) MEDICAL IMAGE SEGMENTATION USING DEEP LEARNING MODELS TRAINED WITH RANDOM DROPOUT AND/OR STANDARDIZED INPUTS

(71) Applicant: The Medical College of Wisconsin, Inc., Milwaukee, WI (US)

(72) Inventors: Robert Thaddeus Wujek, Milwaukee, WI (US); Kathleen Marie Schmainda, Elm Grove, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 397 days.

(21) Appl. No.: 17/284,715

(22) PCT Filed: Oct. 11, 2019

(86) PCT No.: PCT/US2019/055824
§ 371 (c)(1),
(2) Date: Apr. 12, 2021

(87) PCT Pub. No.: WO2020/077202
PCT Pub. Date: Apr. 16, 2020

(65) Prior Publication Data
US 2021/0358629 A1    Nov. 18, 2021

Related U.S. Application Data

(60) Provisional application No. 62/745,167, filed on Oct. 12, 2018.

(51) Int. Cl.
*G06K 9/62* (2022.01)
*G16H 50/20* (2018.01)
(Continued)

(52) U.S. Cl.
CPC ............... *G16H 50/20* (2018.01); *G06N 3/08* (2013.01); *G06T 7/0012* (2013.01); *G06T 7/143* (2017.01);
(Continued)

(58) Field of Classification Search
CPC ........ G16H 50/20; G16H 30/20; G16H 30/40; G06N 3/08; G06N 3/045; G06N 3/082;
(Continued)

(56) References Cited

U.S. PATENT DOCUMENTS 10,713,537 B2 * 7/2020 Heide .................. G06V 10/764
2018/0218502 A1 * 8/2018 Golden ..................... G06T 7/11
(Continued)

FOREIGN PATENT DOCUMENTS

WO     WO-2018048575 A1 * 3/2018 ............... A61N 5/10

*Primary Examiner* — Xin Jia
(74) *Attorney, Agent, or Firm* — Quarles & Brady LLP

(57) ABSTRACT

Systems and methods are described for segmenting medical images, such as magnetic resonance images, using a deep learning model that has been trained using random dropped inputs, standardized inputs, or both. Medical images can be segmented based on anatomy, physiology, pathology, other properties or characteristics represented in the medical images, or combinations thereof. As one example, multi-contrast magnetic resonance images are input to the trained deep learning model in order to generate multiple segmented medical images, each representing a different segmentation class.

16 Claims, 6 Drawing Sheets

(51) Int. Cl.
- *G06T 7/143* (2017.01)
- *G16H 30/20* (2018.01)
- *G16H 30/40* (2018.01)
- *G06N 3/08* (2023.01)
- *G06T 7/00* (2017.01)

(52) U.S. Cl.
CPC .............. *G16H 30/20* (2018.01); *G16H 30/40* (2018.01); *G06T 2207/10088* (2013.01); *G06T 2207/20084* (2013.01)

(58) Field of Classification Search
CPC ................... G06T 7/0012; G06T 7/143; G06T 2207/10088; G06T 2207/20084; G06T 2207/20081; G06T 2207/30016; G06T 7/11
See application file for complete search history.

(56) References Cited

U.S. PATENT DOCUMENTS

| | | | |
|---|---|---|---|
| 2019/0030370 A1* | 1/2019 | Hibbard | A61N 5/1067 |
| 2019/0175952 A1* | 6/2019 | Hissoiny | A61N 5/1049 |

* cited by examiner

MEDICAL IMAGE SEGMENTATION USING DEEP LEARNING MODELS TRAINED WITH RANDOM DROPOUT AND/OR STANDARDIZED INPUTS

CROSS-REFERENCE TO RELATED APPLICATIONS

This application is a 371 U.S. National Phase application of PCT/US2019/055824, filed Oct. 11, 2019, which claims the benefit of U.S. Provisional Patent Application Ser. No. 62/745,167, filed on Oct. 12, 2018, and entitled "MEDICAL IMAGE SEGMENTATION USING DEEP LEARNING MODELS TRAINED WITH RANDOM DROPOUT AND/OR STANDARDIZED INPUTS," which is herein incorporated by reference in its entirety.

STATEMENT REGARDING FEDERALLY SPONSORED RESEARCH

This invention was made with government support under CA176110 awarded by the National Institutes of Health. The government has certain rights in the invention.

BACKGROUND

In recent years, machine learning methods have shown much promise for the automated segmentation of brain and tumors in medical imaging, resulting in substantial improvements in both accuracy and speed. However, few methods have been refined to the point of FDA approval. One reason for this is that these techniques are prone to failure when applied to data that is not well represented in the training process. For example, a model may be trained to segment tumor regions using a combination of MRI and PET scans but will be unable to perform effectively when only one or the other is available.

Similarly, a model trained with data acquired with one MRI scanner may not test well with data acquired with another. This is because machine learning models are sensitive to variability of data from different scanners, even when acquisition methods are identical.

This presents the need for segmentation models that can function using variable subsets of data as opposed to traditional models which require datasets that meet rigid specifications.

This also presents the motivation for using image standardization or calibration methods in combination with segmentation models that can function without training a new model for every scanner. Note, the image standardization we refer to is different than the imaging community's efforts to homogenize acquisition settings or restrict acquisition to a single platform. Rather standardization refers to a unique machine-learned algorithm that is trained once and then applied to all subsequent input images. The result is images of the same type having the same intensity levels for a given tissue type.

SUMMARY OF THE DISCLOSURE

The present disclosure addresses the aforementioned drawbacks by providing a computer-implemented method for training and utilizing a deep convolutional neural network ("DCNN") to segment medical images, such as magnetic resonance images acquired with a magnetic resonance imaging ("MRI") system. The DCNN is trained by modifying the DCNN to include one or more dropout layers and updating the DCNN by inputting training data to the DCNN to generate output data, calculating an error between the training data and the output data, and updating weights in the DCNN based on the calculated error. This process is repeated until a stopping criterion is satisfied, at which time the one or more dropout layers is removed from the updated DCNN. The updated DCNN is then stored as the trained DCNN. Segmented medical images are generated from the medical image data by inputting the medical images to the trained DCNN, including passing the medical images to a contracting path of the DCNN, generating output, and passing the output from the contracting path of the DCNN to an expanding path of the DCNN, generating the segmented medical images.

It is another aspect of the present disclosure to provide a system for generating segmented medical image data. The system includes a memory and a processor. The memory has stored thereon medical image data and a trained deep learning model. The stored trained deep learning model that was trained by iteratively updating the deep learning model until a stopping criterion was satisfied by inputting training data comprising at least one of randomly dropped inputs or standardized inputs to the deep learning model in order to generate output data; calculating an error between the training data and the output data; and updating weights in the deep learning model based on the calculated error. The processor, which is in communication with the memory, is configured to retrieve the medical image data and the trained deep learning model from the memory and to generate segmented medical image data by inputting the medical image data to the trained deep learning model, generating output as the segmented medical image data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
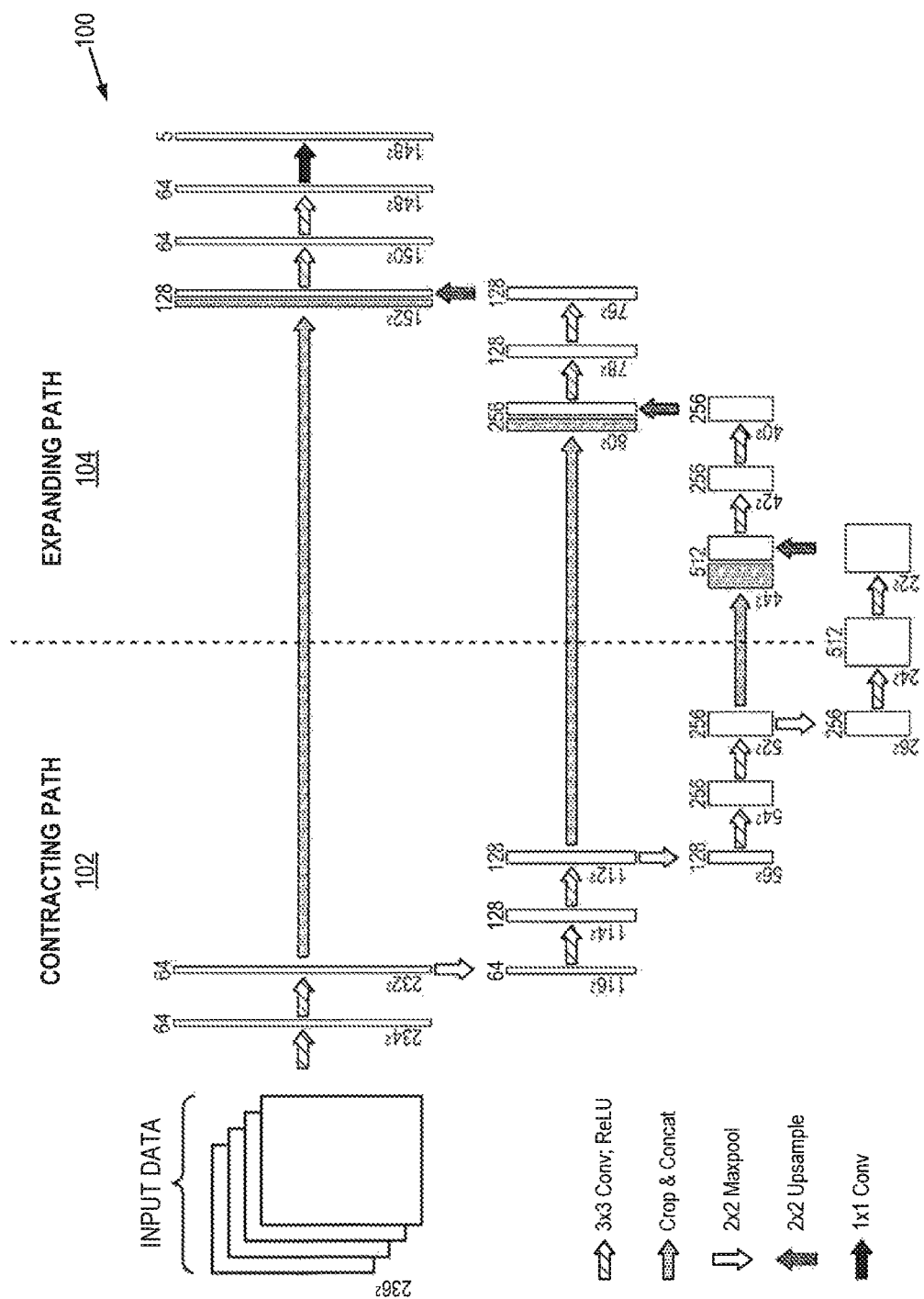
FIG. 1 is an example of a deep convolutional neural network ("DCNN") architecture that can be implemented by the systems and methods described in the present disclosure.

Described here are systems and methods for segmenting medical images, such as magnetic resonance images, using a machine learning algorithm, such as a machine learning algorithm implementing a deep learning model, that has been trained using random dropped inputs, standardized inputs, or both. The systems and methods described in the present disclosure can be used to segment medical images based on anatomy, physiology, pathology, other properties or characteristics represented in the medical images, or combinations thereof. For instance, medical images depicting a subject's brain can be segmented into different tissue types (e.g., gray matter, white matter, cerebrospinal fluid). As another example, medical images can be segmented based on pathology, such as by segmenting a tumor from surrounding tissues. In such instances, a tumor can also be segmented into different components (e.g., to separately segment the tumor margin).

As noted, using the systems and methods described in the present disclosure, medical images are segmented by inputting the images to a deep learning model that has been trained using random dropped inputs, standardized inputs, or combinations thereof.

By training the deep learning model using random subsets of inputs (e.g., by random dropout of inputs during the training process), the model is trained to learn the segmentation process under a range of input combinations. Previous deep learning-based segmentation methods required a new model to be trained for each type of input or combination of inputs. Moreover, current deep learning segmentation methods require image sets to meet very specific conditions. If one or more of the image types is unusable due to poor acquisition or exclusion from imaging protocol, the segmentation fails. Using random dropped inputs to train the deep learning model for segmentation can overcome this shortcoming, enabling an improvement in the ability of the deep learning model (and thus the computer system implementing the deep learning model) to segment medical images. For instance, the systems and methods described in the present disclosure can be used to accurately segment medical images even under conditions where an input data set is incomplete.

By training the deep learning model using standardized inputs (e.g., by incorporating standardization methods applied to the inputs), the model is trained to learn the segmentation process despite variability of data acquired from different medical imaging systems, such as different MRI scanners. Previous deep learning-based segmentation methods required a new model to be trained for each medical imaging system (e.g., each MRI scanner). Thus, current deep learning segmentation methods do not account for multi-site variability without training a new model for each acquisition source. Using standardized inputs to train the deep learning model for segmentation can overcome this shortcoming, enabling an improvement in the ability of the deep learning model (and thus the computer system implementing the deep learning model) to segment medical images.

The deep learning model implemented in the systems and methods described in the present disclosure can be any suitable deep learning model. In some instances, the deep learning model implements a neural network architecture. The neural network architecture may be a convolutional neural network architecture. As one example, the deep learning model can be a deep convolutional neural network ("DCNN") architecture that is based in part on a U-net convolutional neural network architecture.

Unlike a U-net architecture, which typically has one input image and two outputs representative of a binary pixel classification (e.g., a yes or no pixel classification), the DCNN architecture described in the present disclosure takes a plurality of input images (e.g., four inputs) and has more than two outputs (e.g., five outputs). For instance, the DCNN architecture implemented in the systems and methods described in the present disclosure can take M>1 inputs and provide N>2 outputs. With this configuration, each pixel can be classified as belonging to one out N different segmentation classes or categories, which can effectively segment several different tissue types at the same time. This DCNN architecture can operate on fewer starting dimensions and can implement fewer blocks, which can reduce the computation complexity relative to traditional U-net architectures. In some other configurations, it may also be possible to use fewer inputs (e.g., M=1), fewer outputs (e.g., N≥1), or both.

FIG. 1 is a diagram of an example deep convolution neural network ("DCNN") architecture that can be implemented with the systems and methods described in the present disclosure. The DCNN 100 generally includes a contracting path 102 and an expanding path 104.

The contracting path 102 generally implements a convolution neural network. For instance, the contracting path 102 can include repeated application of convolution layers (e.g., 3×3 convolutions) each followed by a nonlinear layer, which may be a rectified linear unit ("ReLU"). The output of each convolutional layer is a feature map that is passed to the nonlinear layer. Each feature map generally represents a particular feature extracted at all locations on the input. Each nonlinear layer is followed by a downsampling layer, which may be a pooling layer, such as a max pooling layer (e.g., a 2×2 max pooling operation), an average pooling layer, an L2-norm pooling layer, or so on. The output of each nonlinear layer is a feature map that is passed to the downsampling layer. At each downsampling step, the number of feature channels in the feature map can be doubled, or otherwise increased. In some implementations, the downsampling layers can be followed by a dropout layer that removes nodes randomly according to a predetermined "dropout rate." In these instances, sparsity is introduced into the model, which effectively reduces the dependence of the model performance on any single node.

The expanding path 104 generally includes an upsampling layer followed by a convolutional layer (e.g., a 2×2 convolution). The output of each upsampling layer is a feature map that is passed to the convolutional layer. At each upsampling step, the number of feature channels in the feature map can be halved, or otherwise reduced. Each upsampled feature map is also concatenated with the corresponding feature map from the contracting path 102. The concatenated feature map is then passed to a convolutional layer (e.g., a 3×3 convolution) followed by a nonlinear layer (e.g., a ReLU). The output of the convolutional layer is a feature map that is passed to the nonlinear layer. The final layer is a convolutional layer (e.g., a 1×1 convolution) that maps each feature channel to the N different segmentation classes. The output of the final convolution layer is N different maps (e.g., logit maps) corresponding to the N different segmentation classes. Each logit map represents the confidence levels that each index belongs to a given class. For a given index, the logit map with the largest value is predicted to be the correct classification for the given index. These logit maps collectively represent the segmented image, and can be combined with class label data to generate one or more segmented images that are labeled with the corresponding segmentation classes.

As noted above, the DCNN 100 may be trained using random dropped inputs. In these instances, one of the M input channels to the model may be deactivated, which effectively removes that contribution of the particular input to the final prediction. By randomly or strategically dropping inputs throughout the training process, the trained DCNN 100 can perform effectively with variable inputs (e.g., all M inputs, fewer than all M inputs). This creates a more robust model as compared to traditionally trained models. After the DCNN 100 has been trained, the one or more dropout layers are removed from the DCNN 100.

Figure 2:
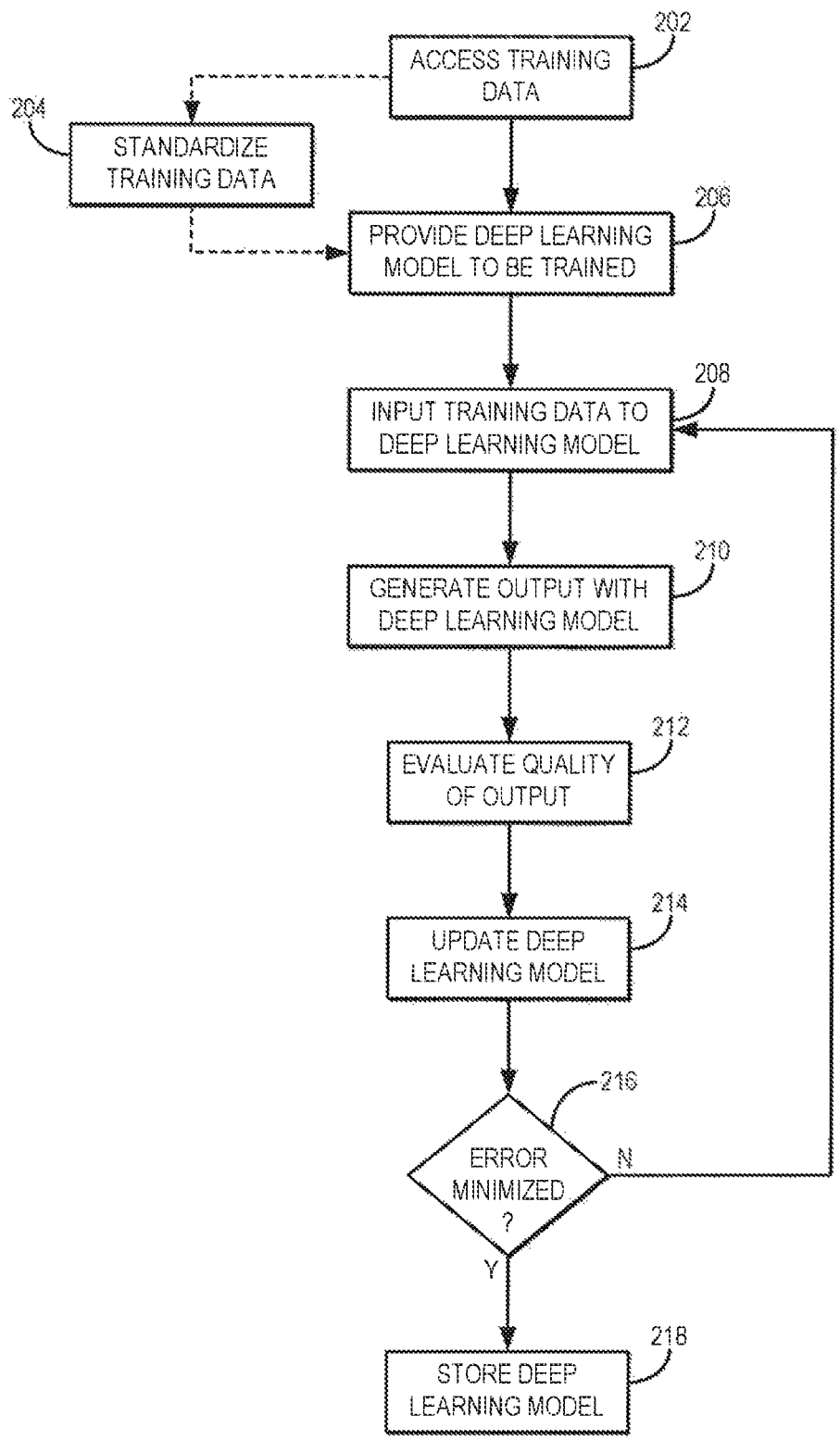
FIG. 2 is a flowchart setting forth the steps of an example method for training a deep learning model, such as a deep convolutional neural network ("DCNN"), for segmenting medical images.

Referring now to FIG. 2, a flowchart is illustrated as setting forth the steps of an example method for training a deep learning model, such as a DCNN, to segment a medical image.

The method includes accessing training data with a computer system, as indicated at step 202. In general, the training data contain medical images, which may include magnetic resonance images. In some instances, the medical images may be labeled images containing labeled components corresponding to one or more different segmentation classes corresponding to different tissues, anatomy, physiology, pathology, or so on. As a non-limiting example, labeled images may include images that depict different labeled anatomical regions, different labeled tissues (e.g., gray matter, white matter, cerebrospinal fluid), or different labeled pathologies (e.g., tumor, tumor margin). It will be appreciated that different labels corresponding to different segmentation classes or categories can also be contained in the labeled images.

Optionally, the training data can be standardized, as indicated at step 204. In general, standardizing the training data may include medical images that have been standardized to reduce variations associated with the medical imaging system used to acquire the medical images. For instance, the medical images could be standardized using the methods described by L. G. Nyul and J. K. Udupa in "On standardizing the MR image intensity scale," *Magnetic Resonance in Medicine,* 1999; 42:1072-1081; or by L. G. Nyul, et al., in "New variants of a method of MRI scale standardization," *IEEE Trans Med Imaging,* 2000; 19:143-150; or by T. R. Jensen and K. M. Schmainda in "Computer-aided detection of brain tumor invasion using multiparametric MRI," *J Magn Reson Imaging,* 2009; 30:481-489; or by D. Bedekar, et al., in "Standardization of relative cerebral blood volume (rCBV) image maps for ease of both inter- and intrapatient comparisons," *Magn Reson Med,* 2010; 64:907-913.

A deep learning model, such as a DCNN, to be trained is then provided to the computer system, as indicated at step 206. As noted above, during the training process, the deep learning model may be a DCNN that is augmented to include one or more dropout layers in the contracting path of the DCNN, which each drop out a random set of activations in that layer. The training data are then input to the deep learning model, as indicated at step 208. The current model of the deep learning model (e.g., the DCNN) then generates an output, as indicated at step 210. The output may include one or more segmented images corresponding to one or more different segmentation classes. The quality of the output is then evaluated at step 212. Evaluating the quality of the output may include passing the output to a loss layer in order to calculate an error. For example, an error between the training data and the output can be computed. The deep learning model is then updated based on the calculated error (e.g., using backpropagation methods based on the calculated error), as indicated at step 214. For instance, the deep learning model can be a DCNN that is updated by updating the weights in the convolutional layers in the DCNN in order to minimize the loss according to the loss function defined in the loss layer. A determination is then made a decision block 216 whether the error has been minimized (e.g., by determining whether an error threshold or other stopping criterion has been satisfied). When the error has been minimized then the deep learning model has been trained and it is stored (e.g., in a memory or other suitable data storage or storage medium) for later use, as indicated at step 218.

Figure 3:
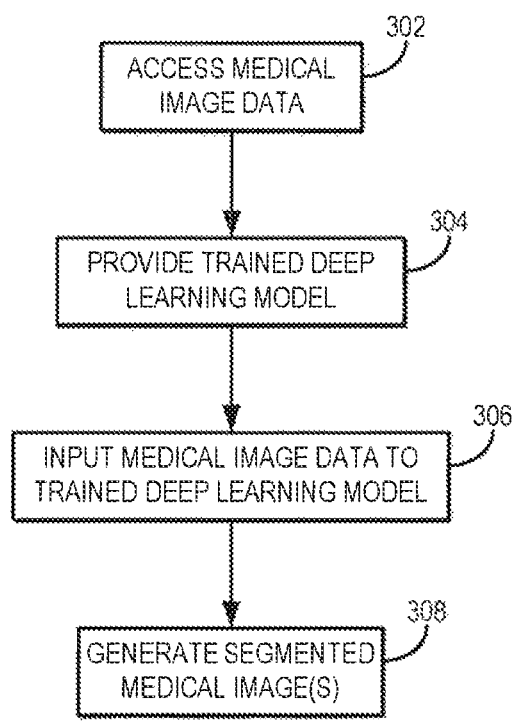
FIG. 3 is a flowchart setting forth the steps of an example method for segmenting medical images using a trained deep learning model.

Referring now to FIG. 3, a flowchart is illustrated as setting forth the steps of an example method for utilizing a trained deep learning model, such as a trained DCNN, to segment a medical image. Medical image data are accessed by a computer system, as indicated at step 302. The medical image data can be accessed by the computer system, for example, by retrieving medical image data stored on a memory or other data storage device or medium. The medical image data can also be accessed by the computer system by acquiring medical image data with a medical imaging system and sending the medical image data from the medical imaging system to the computer system. In some instances, the computer system can form a part of the medical imaging system.

The medical image data generally includes images obtained with a medical imaging system. The medical image data can include medical images corresponding to a plurality of different slices, such that the medical image data are representative of an image volume. In some instances, the medical image data can include more than one medical image for each slice. For example, the medical image data may include medical images acquired at the same slice, but with different contrast weightings, using different acquisition settings, at different times, or combinations thereof.

In some embodiments, the medical image data contain medical images obtained with an MRI system (i.e., magnetic resonance images or images otherwise generated from data acquired with an MRI system). As one example, the medical image data can contain multi-contrast magnetic resonance image data. In these instances, the medical image data contains images obtained with multiple different contrast weightings or using different imaging sequences known in the magnetic resonance imaging arts. Examples of different contrast weightings include T1-weighting, with or without contrast enhancement with a contrast agent; T2-weighting, with or without contrast enhancement with a contrast agent; perfusion weighting; diffusion weighting; and so on. Magnetic resonance images can be also acquired with different imaging techniques that modify the appearance of anatomical or physiological properties. As one non-limiting example, magnetic resonance images can be acquired using fluid attenuation inversion recovery ("FLAIR") to reduce signal from fluid, such as cerebrospinal fluid. As another example, non-contrast enhanced angiography techniques, such as phase contrast imaging or arterial spin labeling, may be used to visualize blood flow or tissue vasculature.

Input data are selected by the computer system, as indicated at step 304. For instance, the computer system is operated to select a number of images from the medical image data to be stored as the input data. As one example, the computer system can select M different images from the MR image data to be stored as the input data. In some implementations, the M different images correspond to the same slice or volume in the subject, but in some other implementations the M different images may correspond to two or more different slices or volumes. The M different images may represent different contrast weightings, as noted above. For instance, the M different images can represent M different contrast weightings for the same slice or volume in the subject, or can represent fewer than M contrast weightings for the same slice or volume, or for multiple different slices or volumes. The M different images may also correspond to M different time points in a time series of image frames and may represent one or more different slices or volumes in the subject. The M different images may also correspond to M different images acquired from the same slice or volume in the subject in a different repetition of a pulse sequence.

A trained deep learning model, which may be a trained DCNN, is selected by the computer system, as indicated at step 306. In some implementations, the trained deep learning model is a DCNN that was trained using a training process during which inputs are randomly dropped. Additionally or alternatively, the trained deep learning model is a DCNN that was trained using standardized inputs.

The medical image data are then input to the trained deep learning model, as indicated at step 308, in order to generate one or more segmented images, as indicated at step 310. The one or more segmented images may include one image for each of a plurality of different segmentation classes, or may include a single image in which each of a plurality of different segmentation classes is identified (e.g., by overlaying a different contour for each segmentation class onto the image).

As noted above, inputting the medical image data to the trained deep learning model that is a DCNN in order to generate one or more segmented images may include inputting a plurality of medical images (e.g., N medical images) to a contracting path of the DCNN. The medical images are input to a convolutional layer, generating an output. The output of the convolutional layer is passed to a nonlinear layer, which may implement an ReLU, generating an output. The output of the nonlinear layer is passed to a downsampling layer and also stored to be concatenated with an output of a corresponding upsampling layer in an expanding path of the DCNN. The downsampling layer may be a pooling layer, such as a max pooling layer, an average pooling layer, an L2-norm pooling layer, or so on.

The output of the final layer in the contracting path is passed to a convolutional layer in the expanding path, generating an output. The output of this convolution layer is passed to a nonlinear layer, generating an output. The output of this nonlinear layer is passed to an upsampling layer, generating an output. As noted above, the output of this upsampling layer is concatenated with the output from the nonlinear layer in the corresponding level of the contracting path. The concatenated output is passed to a convolutional layer, generating an output. This process is repeated until the last level of the expanding path, where the output of the nonlinear layer in that level is passed to a final convolutional layer, which may be a classification layer, generating output as the one or more segmented medical images.

EXAMPLE

Dataset

In an example study, a DCNN was trained and utilized to generate segmented medical images. This study was performed using magnetic resonance images obtained from 220 high grade glioma cases. Each image set included T2-weighted images, T1-weighted images, T1-weighted images with contrast enhancement provided by a contrast agent, and FLAIR images. Each image set also included radiologist annotated segmentations for edema, necrosis, non-enhancing tumor, and enhancing tumor. Prior to training, the imaging data sets were normalized using a robust deviation method.

Model Architecture

The DCNN architecture used in this example study included 7 blocks. Input resolution was $236^2$ and the output was expanded to generate 5 channels for classification: 4 annotated tissues, plus background. Additionally, 7 types of dropout were applied to the inputs in order to train models under different conditions: a model trained with all contrast weightings; a single random input is dropped from each image set; a single random input is dropped from 80% of the image sets; and a single contrast weighting is dropped from the entire dataset, repeated for each modality (T2, T1, T1+C, FLAIR).

Training

Training of the DCNN implemented cross entropy with an L2 regularizer on all trainable weights as a cost function, and RMSProp was used for backpropogation (decay=0.9 and momentum=0.9). The DCNN models were trained over the entire training set in batches of 20 slices for a total of 1,364 epochs.

Analysis

Predicted segmentations were grouped to generate "Whole Tumor," "Tumor Core," and "Active Tumor" regions-of-interest.

Systems

Figure 4:
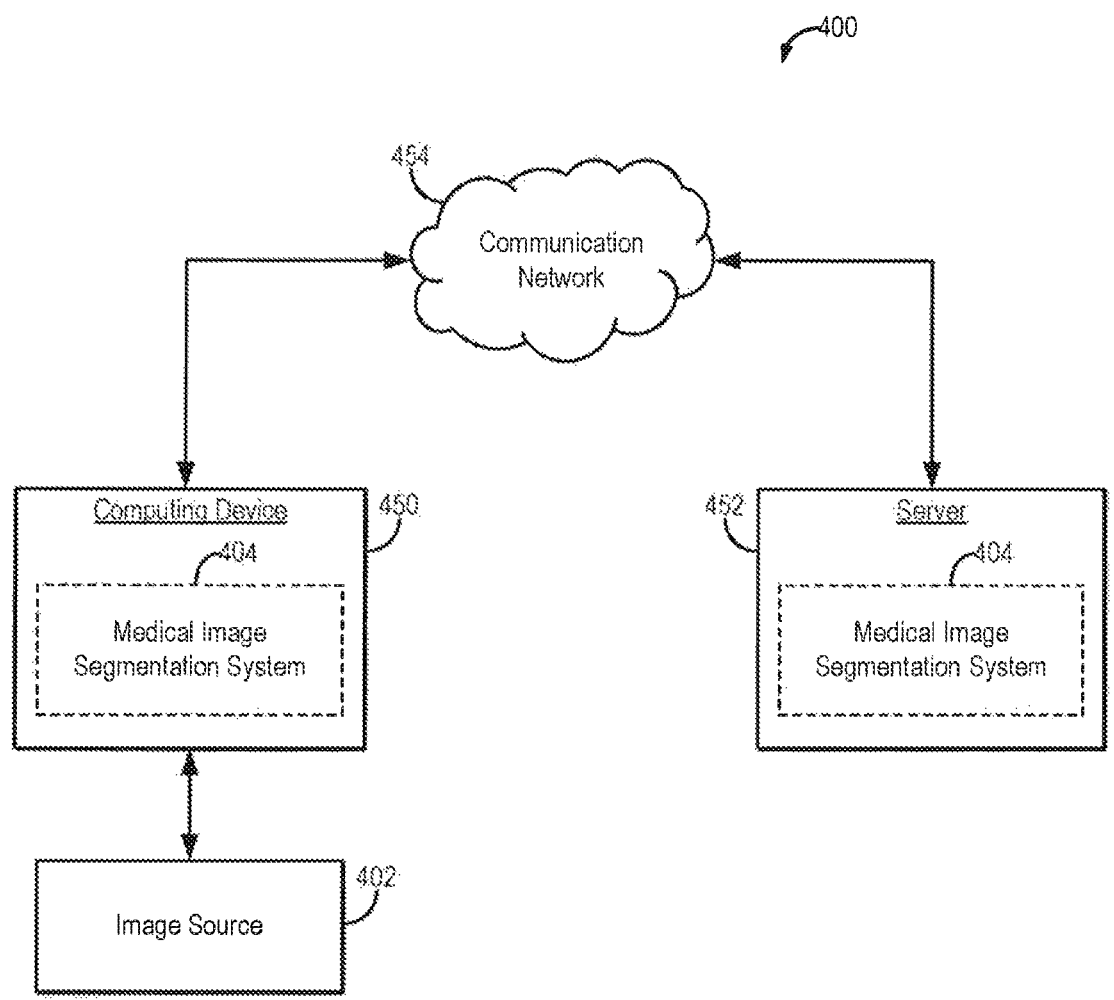
FIG. 4 is a block diagram of an example system that can implement the DCNN to segment medical images.

Referring now to FIG. 4, an example of a system 400 for segmenting medical images in accordance with some embodiments of the systems and methods described in the present disclosure is shown. As shown in FIG. 4, a computing device 450 can receive one or more types of data (e.g., training data, medical image data) from image source 402, which may be a medical image source. In some embodiments, computing device 450 can execute at least a portion of a medical image segmentation system 404 to train and utilize a deep learning model to segment one or more medical images from medical image data received from the image source 402.

Additionally or alternatively, in some embodiments, the computing device 450 can communicate information about data received from the image source 402 to a server 452 over a communication network 454, which can execute at least a portion of the medical image segmentation system 404 to train and utilize a deep learning model to segment one or more medical images from medical image data received from the image source 402. In such embodiments, the server 452 can return information to the computing device 450 (and/or any other suitable computing device) indicative of an output of the medical image segmentation system 404 to train and utilize a deep learning model to segment one or more medical images from medical image data received from the image source 402.

In some embodiments, computing device 450 and/or server 452 can be any suitable computing device or combination of devices, such as a desktop computer, a laptop computer, a smartphone, a tablet computer, a wearable computer, a server computer, a virtual machine being executed by a physical computing device, and so on. The computing device 450 and/or server 452 can also reconstruct images from the data.

In some embodiments, image source 402 can be any suitable source of image data (e.g., measurement data, images reconstructed from measurement data), such as an MRI system, another computing device (e.g., a server storing image data), and so on. In some embodiments, image source 402 can be local to computing device 450. For example, image source 402 can be incorporated with computing device 450 (e.g., computing device 450 can be configured as part of a device for capturing, scanning, and/or storing images). As another example, image source 402 can be connected to computing device 450 by a cable, a direct wireless link, and so on. Additionally or alternatively, in some embodiments, image source 402 can be located locally and/or remotely from computing device 450, and can communicate data to computing device 450 (and/or server 452) via a communication network (e.g., communication network 454).

In some embodiments, communication network 454 can be any suitable communication network or combination of communication networks. For example, communication network 454 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 4 can each be any suitable communications link or combination of communications links, such as wired links, fiber optic links, Wi-Fi links, Bluetooth links, cellular links, and so on.

Figure 5:
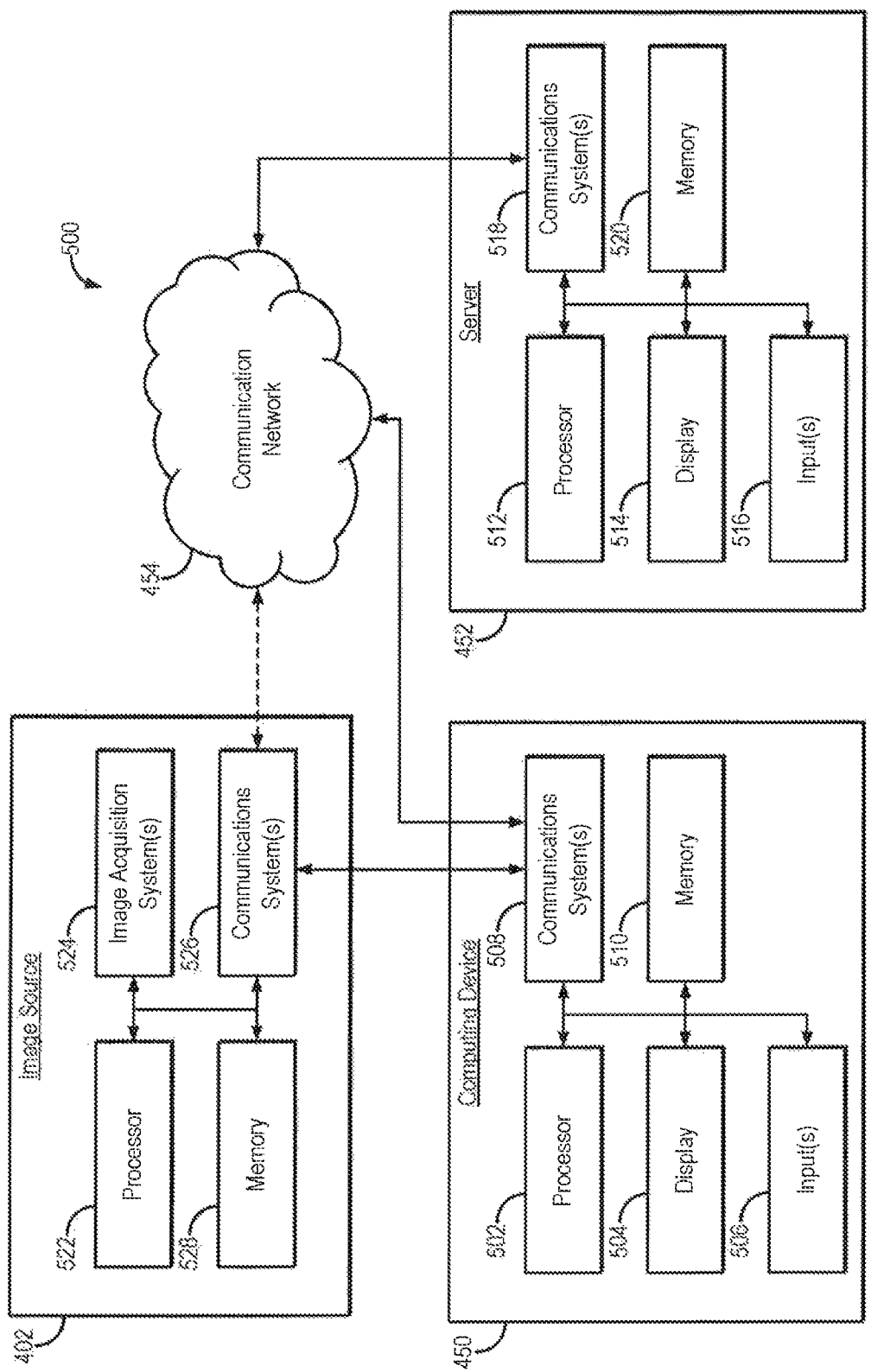
FIG. 5 is a block diagram of example hardware components of the system shown in FIG. 4.

Referring now to FIG. 5, an example of hardware 500 that can be used to implement image source 402, computing device 450, and server 452 in accordance with some embodiments of the systems and methods described in the present disclosure is shown. As shown in FIG. 5, in some embodiments, computing device 450 can include a processor 502, a display 504, one or more inputs 506, one or more communication systems 508, and/or memory 510. In some embodiments, processor 502 can be any suitable hardware processor or combination of processors, such as a central processing unit ("CPU"), a graphics processing unit ("GPU"), and so on. In some embodiments, display 504 can include any suitable display devices, such as a computer monitor, a touchscreen, a television, and so on. In some embodiments, inputs 506 can include any suitable input devices and/or sensors that can be used to receive user input, such as a keyboard, a mouse, a touchscreen, a microphone, and so on.

In some embodiments, communications systems 508 can include any suitable hardware, firmware, and/or software for communicating information over communication network 454 and/or any other suitable communication networks. For example, communications systems 508 can include one or more transceivers, one or more communication chips and/or chip sets, and so on. In a more particular example, communications systems 508 can include hardware, firmware and/or software that can be used to establish a Wi-Fi connection, a Bluetooth connection, a cellular connection, an Ethernet connection, and so on.

In some embodiments, memory 510 can include any suitable storage device or devices that can be used to store instructions, values, data, or the like, that can be used, for example, by processor 502 to present content using display 504, to communicate with server 452 via communications system(s) 508, and so on. Memory 510 can include any suitable volatile memory, non-volatile memory, storage, or any suitable combination thereof. For example, memory 510 can include RAM, ROM, EEPROM, one or more flash drives, one or more hard disks, one or more solid state drives, one or more optical drives, and so on. In some embodiments, memory 510 can have encoded thereon, or otherwise stored therein, a computer program for controlling operation of computing device 450. In such embodiments, processor 502 can execute at least a portion of the computer program to present content (e.g., images, user interfaces, graphics, tables), receive content from server 452, transmit information to server 452, and so on.

In some embodiments, server 452 can include a processor 512, a display 514, one or more inputs 516, one or more communications systems 518, and/or memory 520. In some embodiments, processor 512 can be any suitable hardware processor or combination of processors, such as a CPU, a GPU, and so on. In some embodiments, display 514 can include any suitable display devices, such as a computer monitor, a touchscreen, a television, and so on. In some embodiments, inputs 516 can include any suitable input devices and/or sensors that can be used to receive user input, such as a keyboard, a mouse, a touchscreen, a microphone, and so on.

In some embodiments, communications systems 518 can include any suitable hardware, firmware, and/or software for communicating information over communication network 454 and/or any other suitable communication networks. For example, communications systems 518 can include one or more transceivers, one or more communication chips and/or chip sets, and so on. In a more particular example, communications systems 518 can include hardware, firmware and/or software that can be used to establish a Wi-Fi connection, a Bluetooth connection, a cellular connection, an Ethernet connection, and so on.

In some embodiments, memory 520 can include any suitable storage device or devices that can be used to store instructions, values, data, or the like, that can be used, for example, by processor 512 to present content using display 514, to communicate with one or more computing devices 450, and so on. Memory 520 can include any suitable volatile memory, non-volatile memory, storage, or any suitable combination thereof. For example, memory 520 can include RAM, ROM, EEPROM, one or more flash drives, one or more hard disks, one or more solid state drives, one or more optical drives, and so on. In some embodiments, memory 520 can have encoded thereon a server program for controlling operation of server 452. In such embodiments, processor 512 can execute at least a portion of the server program to transmit information and/or content (e.g., data, images, a user interface) to one or more computing devices 450, receive information and/or content from one or more computing devices 450, receive instructions from one or more devices (e.g., a personal computer, a laptop computer, a tablet computer, a smartphone), and so on.

In some embodiments, image source 402 can include a processor 522, one or more image acquisition systems 524, one or more communications systems 526, and/or memory 528. In some embodiments, processor 522 can be any suitable hardware processor or combination of processors, such as a CPU, a GPU, and so on. In some embodiments, the one or more image acquisition systems 524 are generally configured to acquire data, images, or both, and can include an MRI system or one or more radio frequency ("RF") coils used in an MRI system. Additionally or alternatively, in some embodiments, one or more image acquisition systems 524 can include any suitable hardware, firmware, and/or software for coupling to and/or controlling operations of an MRI system. In some embodiments, one or more portions of the one or more image acquisition systems 524 can be removable and/or replaceable.

Note that, although not shown, image source 402 can include any suitable inputs and/or outputs. For example, image source 402 can include input devices and/or sensors that can be used to receive user input, such as a keyboard, a mouse, a touchscreen, a microphone, a trackpad, a trackball, and so on. As another example, image source 402 can include any suitable display devices, such as a computer monitor, a touchscreen, a television, etc., one or more speakers, and so on.

In some embodiments, communications systems 526 can include any suitable hardware, firmware, and/or software for communicating information to computing device 450 (and, in some embodiments, over communication network 454 and/or any other suitable communication networks). For example, communications systems 526 can include one or more transceivers, one or more communication chips and/or chip sets, and so on. In a more particular example, communications systems 526 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 528 can include any suitable storage device or devices that can be used to store instructions, values, data, or the like, that can be used, for example, by processor 522 to control the one or more image acquisition systems 524, and/or receive data from the one or more image acquisition systems 524; to images from data; present content (e.g., images, a user interface) using a display; communicate with one or more computing devices 450; and so on. Memory 528 can include any suitable volatile memory, non-volatile memory, storage, or any suitable combination thereof. For example, memory 528 can include RAM, ROM, EEPROM, one or more flash drives, one or more hard disks, one or more solid state drives, one or more optical drives, and so on. In some embodiments, memory 528 can have encoded thereon, or otherwise stored therein, a program for controlling operation of image source 402. In such embodiments, processor 522 can execute at least a portion of the program to generate images, transmit information and/or content (e.g., data, images) to one or more computing devices 450, receive information and/or content from one or more computing devices 450, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 6:
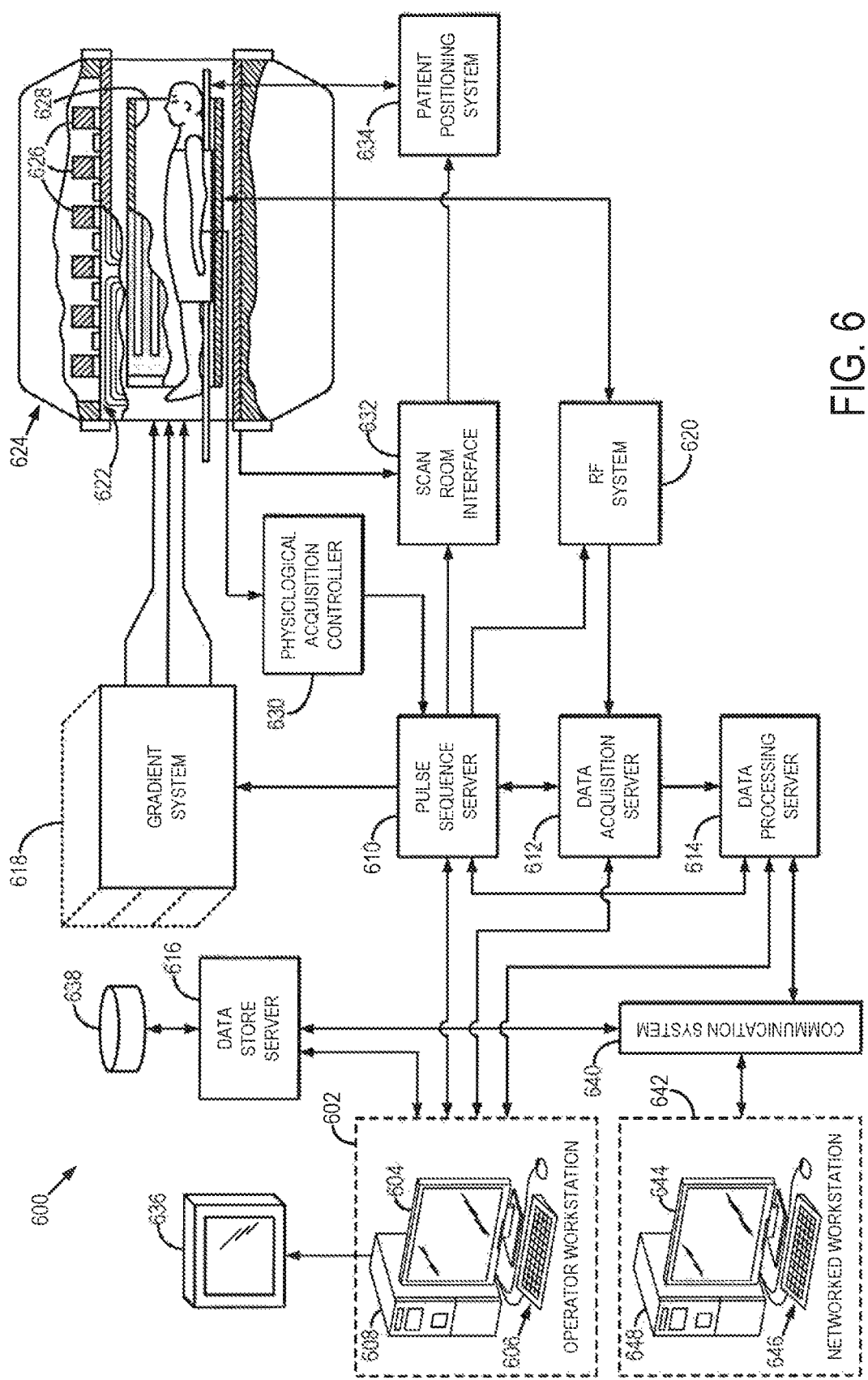
FIG. 6 is a block diagram of an example magnetic resonance imaging ("MRI") system, which can implement the systems and methods described in the present disclosure.

Referring particularly now to FIG. 6, an example of an MRI system 600 that can implement the methods described here is illustrated. The MRI system 600 includes an operator workstation 602 that may include a display 604, one or more input devices 606 (e.g., a keyboard, a mouse), and a processor 608. The processor 608 may include a commercially available programmable machine running a commercially available operating system. The operator workstation 602 provides an operator interface that facilitates entering scan parameters into the MRI system 600. The operator workstation 602 may be coupled to different servers, including, for example, a pulse sequence server 610, a data acquisition server 612, a data processing server 614, and a data store server 616. The operator workstation 602 and the servers 610, 612, 614, and 616 may be connected via a communication system 640, which may include wired or wireless network connections.

The pulse sequence server 610 functions in response to instructions provided by the operator workstation 602 to operate a gradient system 618 and a radiofrequency ("RF") system 620. Gradient waveforms for performing a prescribed scan are produced and applied to the gradient system 618, which then excites gradient coils in an assembly 622 to produce the magnetic field gradients $G_x$, $G_y$, and $G_z$ that are used for spatially encoding magnetic resonance signals. The gradient coil assembly 622 forms part of a magnet assembly 624 that includes a polarizing magnet 626 and a whole-body RF coil 628.

RF waveforms are applied by the RF system 620 to the RF coil 628, or a separate local coil to perform the prescribed magnetic resonance pulse sequence. Responsive magnetic resonance signals detected by the RF coil 628, or a separate local coil, are received by the RF system 620. The responsive magnetic resonance signals may be amplified, demodulated, filtered, and digitized under direction of commands produced by the pulse sequence server 610. The RF system 620 includes an RF transmitter for producing a wide variety of RF pulses used in MRI pulse sequences. The RF transmitter is responsive to the prescribed scan and direction from the pulse sequence server 610 to produce RF pulses of the desired frequency, phase, and pulse amplitude waveform. The generated RF pulses may be applied to the whole-body RF coil 628 or to one or more local coils or coil arrays.

The RF system 620 also includes one or more RF receiver channels. An RF receiver channel includes an RF preamplifier that amplifies the magnetic resonance signal received by the coil 628 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (1);$$

and the phase of the received magnetic resonance signal may also be determined according to the following relationship:

$$\varphi = \tan^{-1}\left(\frac{Q}{I}\right). \quad (2)$$

The pulse sequence server 610 may receive patient data from a physiological acquisition controller 630. By way of example, the physiological acquisition controller 630 may receive signals from a number of different sensors connected to the patient, including electrocardiograph ("ECG") signals from electrodes, or respiratory signals from a respiratory bellows or other respiratory monitoring devices. These signals may be used by the pulse sequence server 610 to synchronize, or "gate," the performance of the scan with the subject's heart beat or respiration.

The pulse sequence server 610 may also connect to a scan room interface circuit 632 that receives signals from various sensors associated with the condition of the patient and the magnet system. Through the scan room interface circuit 632, a patient positioning system 634 can receive commands to move the patient to desired positions during the scan.

The digitized magnetic resonance signal samples produced by the RF system 620 are received by the data acquisition server 612. The data acquisition server 612 operates in response to instructions downloaded from the operator workstation 602 to receive the real-time magnetic resonance data and provide buffer storage, so that data is not lost by data overrun. In some scans, the data acquisition server 612 passes the acquired magnetic resonance data to the data processing server 614. In scans that require information derived from acquired magnetic resonance data to control the further performance of the scan, the data acquisition server 612 may be programmed to produce such information and convey it to the pulse sequence server 610. For example, during pre-scans, magnetic resonance data may be acquired and used to calibrate the pulse sequence performed by the pulse sequence server 610. As another example, navigator signals may be acquired and used to adjust the operating parameters of the RF system 620 or the gradient system 618, or to control the view order in which k-space is sampled. In still another example, the data acquisition server 612 may also process magnetic resonance signals used to detect the arrival of a contrast agent in a magnetic resonance angiography ("MRA") scan. For example, the data acquisition server 612 may acquire magnetic resonance data and processes it in real-time to produce information that is used to control the scan.

The data processing server 614 receives magnetic resonance data from the data acquisition server 612 and processes the magnetic resonance data in accordance with instructions provided by the operator workstation 602. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 614 are conveyed back to the operator workstation 602 for storage. Real-time images may be stored in a data base memory cache, from which they may be output to operator display 604 or a display 636. Batch mode images or selected real time images may be stored in a host database on disc storage 638. When such images have been reconstructed and transferred to storage, the data processing server 614 may notify the data store server 616 on the operator workstation 602. The operator workstation 602 may be used by an operator to archive the images, produce films, or send the images via a network to other facilities.

The MRI system 600 may also include one or more networked workstations 642. For example, a networked workstation 642 may include a display 644, one or more input devices 646 (e.g., a keyboard, a mouse), and a processor 648. The networked workstation 642 may be located within the same facility as the operator workstation 602, or in a different facility, such as a different healthcare institution or clinic.

The networked workstation 642 may gain remote access to the data processing server 614 or data store server 616 via the communication system 640. Accordingly, multiple networked workstations 642 may have access to the data processing server 614 and the data store server 616. In this manner, magnetic resonance data, reconstructed images, or other data may be exchanged between the data processing server 614 or the data store server 616 and the networked workstations 642, such that the data or images may be remotely processed by a networked workstation 642.

The present disclosure has described one or more preferred embodiments, and it should be appreciated that many equivalents, alternatives, variations, and modifications, aside from those expressly stated, are possible and within the scope of the invention.

The invention claimed is:

1. A computer-implemented method for training and utilizing a deep convolutional neural network (DCNN) to segment medical images, the steps of the method comprising:
training the DCNN by:
(i) iteratively updating the DCNN until a stopping criterion is satisfied by:
inputting training data comprising at least one of randomly dropped inputs or standardized inputs to the DCNN in order to generate output data,
calculating an error between the training data and the output data, and
updating weights in the DCNN based on the calculated error;
(ii) storing the updated DCNN as the trained DCNN;
generating segmented medical images from the medical image data by inputting the medical images to the trained DCNN, including:
(i) passing the medical images to a contracting path of the DCNN, generating output;
(ii) passing the output from the contracting path of the DCNN to an expanding path of the DCNN, generating output as the segmented medical images;
wherein the training data comprise multi-contrast magnetic resonance images; and
wherein the multi-contrast magnetic resonance images include contrast weightings comprising at least two of T1-weighting, T1-weighting with contrast enhancement, T2-weighting, T2-weighting with contrast enhancement, fluid attenuation inversion recovery (FLAIR) weighting, diffusion weighting, and perfusion weighting.

2. The method of claim 1, wherein the training data include standardized inputs comprising magnetic resonance images that have been standardized to reduce variations associated with an MRI scanner used to obtain the magnetic resonance images.

3. The method of claim 1, wherein the training data include randomly dropped inputs in which one or more channels in the training data is dropped before inputting the training data to the DCNN.

4. The method of claim 1, wherein passing the medical images to the contracting path of the DCNN includes:

(i) passing the medical images to a convolutional layer, generating output;
(ii) passing the output from the convolutional layer to a nonlinear layer, generating output; and
(iii) passing the output from the nonlinear layer to a downsampling layer, generating output.

5. The method of claim 1, wherein passing the output of the contracting path of the DCNN to the expanding path of the DCNN includes:
(i) passing the output of the contracting path of the DCNN to an upsampling layer, generating output;
(ii) passing the output from the upsampling layer to a convolutional layer, generating output; and
(iii) passing the output from the convolutional layer to a nonlinear layer, generating output.

6. The method of claim 1, wherein passing the medical images to the contracting path of the DCNN includes:
(i) passing the medical images to a convolutional layer, generating output;
(ii) passing the output from the convolutional layer to a nonlinear layer, generating output;
(iii) passing the output from the nonlinear layer to a downsampling layer, generating output; and
wherein passing the output of the contracting path of the DCNN to the expanding path of the DCNN includes:
(i) passing the output of the contracting path of the DCNN to an upsampling layer, generating output;
(ii) concatenating the output from the upsampling layer with the output from a corresponding nonlinear layer in the contracting path, generating a concatenated output;
(iii) passing the concatenated output to a convolutional layer, generating output; and
(iv) passing the output from the convolutional layer to a nonlinear layer, generating output.

7. The method of claim 1, wherein training the DCNN includes modifying the DCNN to include one or more dropout layers before updating the DCNN and removing the one or more dropout layers from the updated DCNN.

8. The method of claim 7, wherein each of the one or more dropout layers drop out a random set of inputs in that layer.

9. The method of claim 1, wherein the training data include both standardized inputs comprising magnetic resonance images that have been standardized to reduce variations associated with an MRI scanner used to obtain the magnetic resonance images, and randomly dropped inputs in which one or more channels in the training data is dropped before inputting the training data to the DCNN.

10. A system for generating segmented medical image data, comprising:
a memory having stored thereon:
medical image data; and
a trained deep learning model that was trained by iteratively updating the deep learning model until a stopping criterion was satisfied by:
inputting training data comprising at least one of randomly dropped inputs or standardized inputs to the deep learning model in order to generate output data,
calculating an error between the training data and the output data, and
updating weights in the deep learning model based on the calculated error;
a processor in communication with the memory and configured to retrieve the medical image data and the trained deep learning model from the memory and to generate segmented medical image data by inputting the medical image data to the trained deep learning model, generating output as the segmented medical image data;
wherein the trained deep learning model is a trained deep convolutional neural network (DCNN); and
wherein inputting the medical image data to the trained DCNN comprises:
(i) passing the medical images to a contracting path of the DCNN, generating output;
(ii) passing the output from the contracting path of the DCNN to an expanding path of the DCNN, generating output as the segmented medical images.

11. The system as recited in claim 10, wherein the medical image data comprise magnetic resonance images.

12. The system as recited in claim 10, wherein the deep learning model was trained using standardized inputs comprising medical image data that were standardized to reduce variations associated with a medical imaging system used to obtain the medical image data.

13. The system as recited in claim 10, wherein the deep learning model was trained using randomly dropped inputs in which one or more channels in the training data were dropped before inputting the training data to the deep learning model.

14. A computer-implemented method for training and utilizing a deep convolutional neural network (DCNN) to segment medical images, the steps of the method comprising:
training the DCNN by:
(i) iteratively updating the DCNN until a stopping criterion is satisfied by:
inputting training data comprising at least one of randomly dropped inputs or standardized inputs to the DCNN in order to generate output data,
calculating an error between the training data and the output data, and
updating weights in the DCNN based on the calculated error;
(ii) storing the updated DCNN as the trained DCNN;
generating segmented medical images from the medical image data by inputting the medical images to the trained DCNN, including:
(i) passing the medical images to a contracting path of the DCNN, generating output;
(ii) passing the output from the contracting path of the DCNN to an expanding path of the DCNN, generating output as the segmented medical images; and
wherein passing the medical images to the contracting path of the DCNN includes:
(i) passing the medical images to a convolutional layer, generating output;
(ii) passing the output from the convolutional layer to a nonlinear layer, generating output; and
(iii) passing the output from the nonlinear layer to a downsampling layer, generating output.

15. The method of claim 14, wherein passing the output of the contracting path of the DCNN to the expanding path of the DCNN includes:
(i) passing the output of the contracting path of the DCNN to an upsampling layer, generating output;
(ii) concatenating the output from the upsampling layer with the output from a corresponding nonlinear layer in the contracting path, generating a concatenated output;
(iii) passing the concatenated output to a convolutional layer, generating output; and
(iv) passing the output from the convolutional layer to a nonlinear layer, generating output.

16. A computer-implemented method for training and utilizing a deep convolutional neural network (DCNN) to segment medical images, the steps of the method comprising:
- training the DCNN by:
  - (i) iteratively updating the DCNN until a stopping criterion is satisfied by:
    - inputting training data comprising at least one of randomly dropped inputs or standardized inputs to the DCNN in order to generate output data,
    - calculating an error between the training data and the output data, and
    - updating weights in the DCNN based on the calculated error;
  - (ii) storing the updated DCNN as the trained DCNN;
- generating segmented medical images from the medical image data by inputting the medical images to the trained DCNN, including:
  - (i) passing the medical images to a contracting path of the DCNN, generating output;
  - (ii) passing the output from the contracting path of the DCNN to an expanding path of the DCNN, generating output as the segmented medical images; and
- wherein passing the output of the contracting path of the DCNN to the expanding path of the DCNN includes:
  - (i) passing the output of the contracting path of the DCNN to an upsampling layer, generating output;
  - (ii) passing the output from the upsampling layer to a convolutional layer, generating output; and
  - (iii) passing the output from the convolutional layer to a nonlinear layer, generating output.

* * * * *